(12) United States Patent
Johnson et al.

(10) Patent No.: US 6,221,037 B1
(45) Date of Patent: Apr. 24, 2001

(54) WRIST TRACTION DEVICE AND METHOD

(75) Inventors: William R. Johnson, Ft. Oglethorpe, GA (US); Ronald K. Johnson; Gordon C. Johnson, both of Murfreesboro, TN (US)

(73) Assignee: JB, Ltd. L.L.C., Ooltewah, TN (US)

( * ) Notice: Subject to any disclaimer, the term of this patent is extended or adjusted under 35 U.S.C. 154(b) by 0 days.

(21) Appl. No.: 09/234,148

(22) Filed: Jan. 18, 1999

Related U.S. Application Data

(63) Continuation of application No. 08/758,210, filed on Nov. 26, 1996, now abandoned.

(51) Int. Cl.[7] .................................................. A61F 5/00
(52) U.S. Cl. ................................................. 602/32; 602/40
(58) Field of Search ................................... 128/845, 846, 128/877, 878, 879, 882, 892; 602/21–23, 32–40

(56) References Cited

U.S. PATENT DOCUMENTS

| | | | | |
|---|---|---|---|---|
| 2,091,643 | * | 8/1937 | Longfellow | 602/40 |
| 5,003,967 | * | 4/1991 | McConnell | 602/21 |
| 5,181,904 | * | 1/1993 | Cook | 602/32 |
| 5,405,312 | * | 4/1995 | Jacobs | 128/892 |

* cited by examiner

*Primary Examiner*—Michael A. Brown
(74) *Attorney, Agent, or Firm*—Douglas T. Johnson; Miller & Martin LLP

(57) ABSTRACT

The present invention provides the method for placing the patient's wrist in traction to alleviate symptoms of carpal tunnel syndrome. The preferred apparatus utilizes a harness to connect the patient's hand to a traction device and a stabilizing attachment to restrain the patient's arm in an anatomically neutral position while isolating the patient's soldier and elbow from the traction device.

12 Claims, 4 Drawing Sheets

WRIST TRACTION DEVICE AND METHOD

This application is a continuation of U.S. patent application Ser. No. 08/758,210 filed Nov. 26, 1996, now abandoned.

FIELD OF THE INVENTION

The present invention provides a method for placing a patient's wrist in traction for the purpose of treating carpal tunnel syndrome, and provides a device such as the illustrated embodiment to hold the patient's arm in an anatomically neutral position while a harness connects the patient's hand to a traction unit.

BACKGROUND OF THE INVENTION

The carpal bones or carpus of the wrist form a deeply concave gutter through which the Median Nerve and flexor tendons pass. The gutter is converted into a tunnel by a ligament, the flexor retinaculum. The crowded long flexor tendons emerge from the carpal tunnel and diverge as they pass down the hand. Usually, the flexor tendons are very slick and glide against each other in the carpal tunnel as the hand is used to grasp objects. However, any condition which causes irritation or inflammation of the tendons or surrounding tissue increases the pressure in the carpal tunnel because the carpal bones and flexor retinaculum ligament are not able to stretch in response to the swelling. Increased pressure in the carpal tunnel begins to squeeze the Median Nerve and the hand will feel numb or ache. This is commonly referred to as carpal tunnel syndrome.

The traditional treatments in the early stages of carpal tunnel syndrome include administering anti-inflammatory medication and splinting or immobilizing the wrist to allow the inflammation and swelling to subside. In more advanced cases, the flexor retinaculum ligament is cut, thereby opening a wall of the carpal tunnel and allowing sufficient space in the wrist to prevent the median nerve from being squeezed.

Obviously, surgery is to be avoided if possible, and to further that goal, the present invention provides an additional method to treat carpal tunnel syndrome, particularly in less advanced cases. The invention preferably consists of an attachment to exiting traction devices that will to enable a patient's wrist to be placed in traction. This wrist traction provides a slight longitudinal separation between the carpal bones in the wrist and the lower heads of the lower arm bones, the radius and the ulna. The slight separation provides some space to relieve compression in the carpal tunnel area.

A need exists to provide a therapeutic device which is distinguishable from a surgical traction splint. Surgical traction splints require surgery and often are associated with the surgical implantation of skeletal pins which is an invasive procedure. Skeletal pins are not natural to the body and may result in infection, or at least discomfort, to the patient. Therapeutic devices are devised to operate without the need to first perform surgery on the patient.

SUMMARY OF THE INVENTION

In accordance with the present invention, an attachment for existing traction devices is provided with three principal components. The first component is an arm restraining segment that immobilizes the patient's arm in an anatomically neutral position and protects the patient's shoulder and elbow from injury during traction. The second component is a sling or harness to engage the patient's hand and connect it to the traction units. The final component is a mechanism to hold the arm immobilizing portion substantially stationary relative to the traction unit so that tension is applied to the patient's wrist.

With this device it is an object and advantage of the invention to apply traction to a patient's wrist to relieve symptoms of carpal tunnel syndrome, other tendon problems and muscle tightness.

It is a further object of the invention to provide a wrist traction attachment that is compatible with existing traction units.

It is a further object of the invention to provide a wrist traction device which may be used by patients with a substantial range of muscular strength and bone size with only simple adjustments.

It is yet another object of the invention to protect the patient's shoulder and elbow from strain during wrist traction and to position the patient's lower arm bones (the radius and ulna) in a generally parallel alignment.

These and other objects and advantages of the invention will become apparent from a study of the drawings and from a review of the specification following hereinafter describing the preferred embodiment which has been given by way of illustration only.

DETAILED DESCRIPTION

Figure 1:
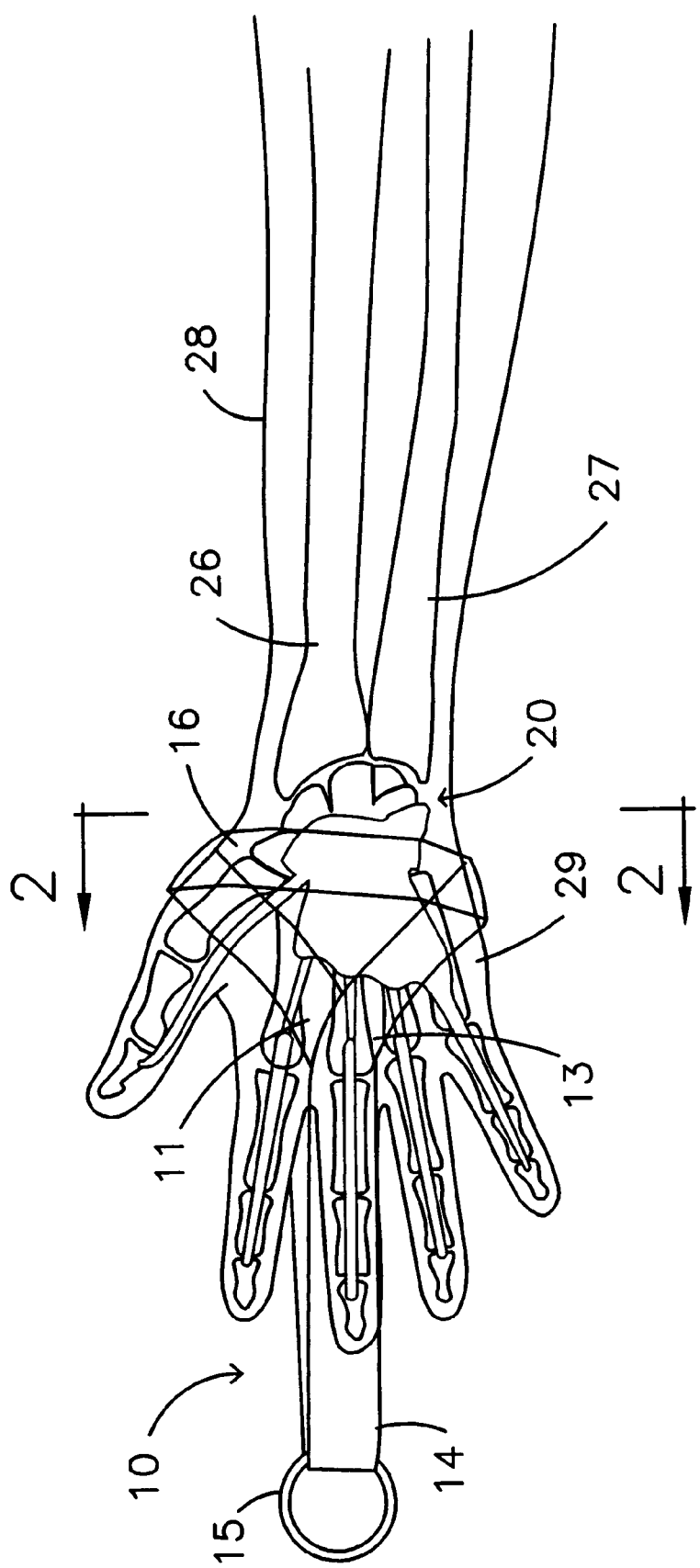
FIG. 1 depicts an anterior view of the palm of hand and lower arm bones showing the flexor sheaths, flexor retinaculum ligament, and the position of a harness to secure the patient's hand according to the present invention.

Turning first to FIG. 1, the lower arm 28 and hand 29 of a patient are illustrated. The lower arm 28 is shown in an anatomically neutral position where the radius 26 and ulna 27 in the lower arm 28 are substantially parallel and do not cross one another. In addition, the patient's hand 29 is shown with a harness 10 according to the present invention. The harness 10 has a midsection 14 upon which rides metal O-ring 15. Harness 10 also has a first end 11 which proceeds around a first loop section 12 (shown in FIG. 3) and back to a first joinder segment 13. In the present embodiment, the first end 11 is simply sewed to the harness at the first joinder segment 13, however, adjustable buckles or straps might be used to allow the harness to adapt to a wider range of patient hand sizes. After the mid-section 14 proceeds from the first joinder segment 13 through O-ring 15, it then proceeds to second joinder segment 16, second loop section 17 and second end 18, all as shown in FIG. 3.

A harness 10 according to the present invention is easily and inexpensively made, however, it will be understood that many variations of this structure will be suitable, so long as they grasp the patient's hand 29 below the interface of the carpal bones 20 with the radius 26 and ulna 27.

Figure 2:
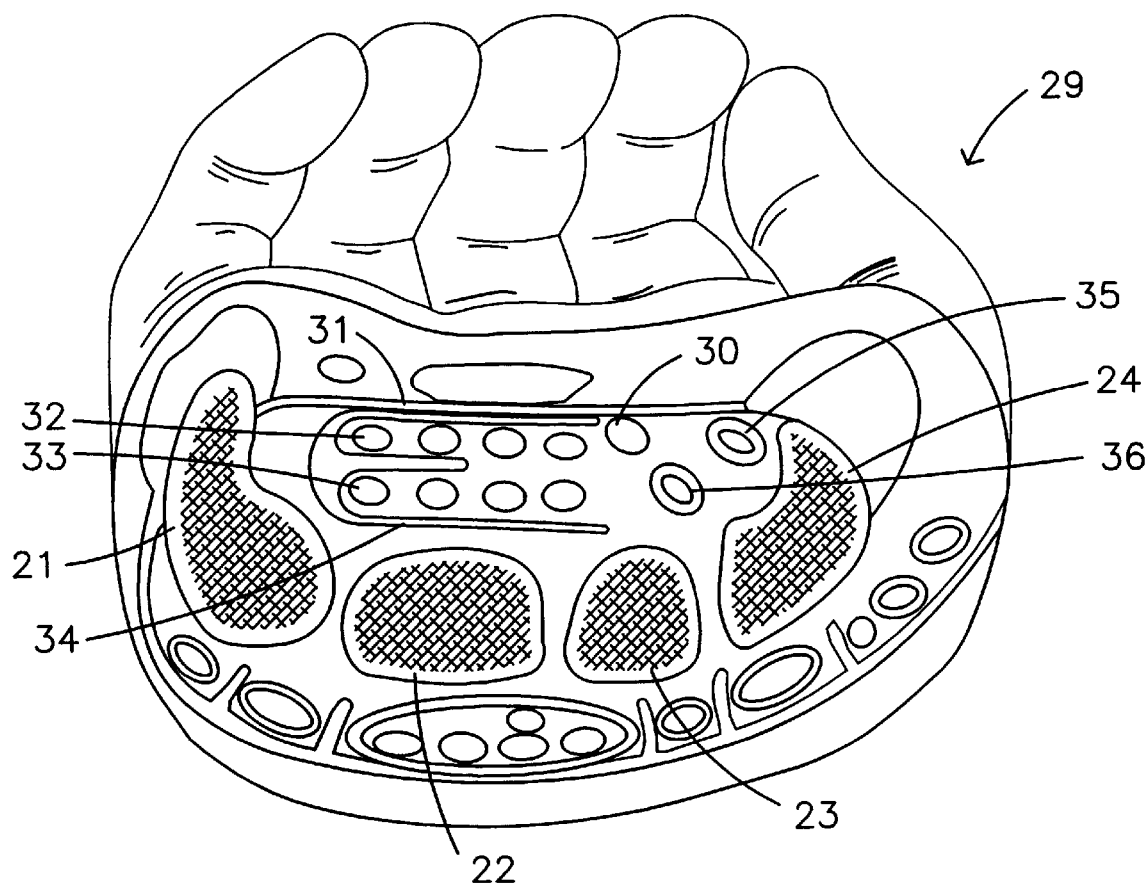
FIG. 2 shows a wrist cross section taken along line 2—2 in FIG. 1 and shows the carpal tunnel formed by carpal bones and the flexor retinaculum ligament.

FIG. 2 provides another illustration of patient's hand 29 taken along the line 2—2 in FIG. 1. Specifically illustrated in FIG. 2 is the gutter formed by carpal bones 20, including hamate 21, capitate 22, trapezoid 23, and ridge of trapezium 24. Several other carpal bones are not illustrated. The top of the gutter is formed by flexor retinaculum 31, which thereby encases the Median Nerve 30 and several flexor tendons including flexor digitorum superficialis 32, flexor digitorum profundis 33, flexor carpi radialis 35, and flexor pollicis longus 36. Flexor synovial sheath 34 also encompasses some of these flexor tendons. From the illustration in FIG. 2, it can be seen how pressure within the tunnel formed by flexor retinaculum 31 and carpal bones 20 will place pressure on median nerve 30.

Figure 3:
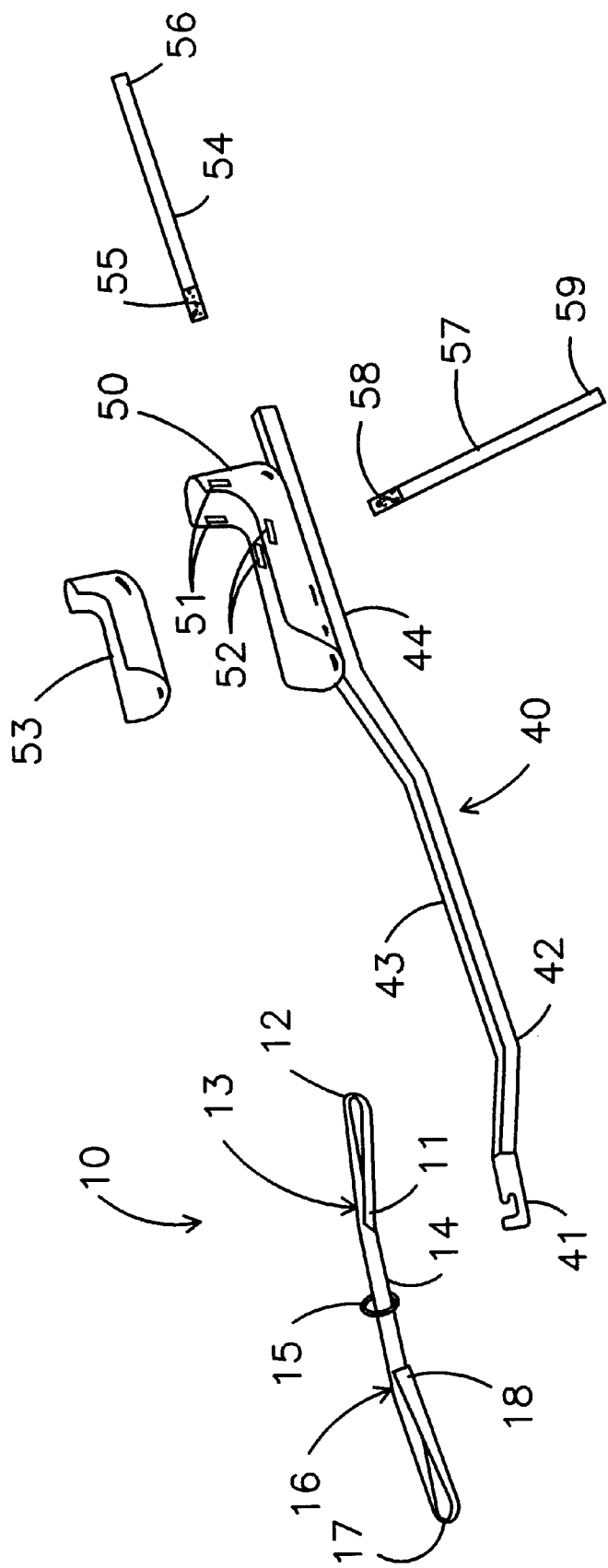
FIG. 3 is a perspective view of the principal components of a preferred embodiment of the invention.

FIG. 3 illustrates a preferred embodiment of the invention including the previously described harness 10 and a patient stabilizer attachment 40. The stabilizer attachment 40 consists primarily of the stabilizer bar 42 and elbow cup 50. The stabilizer bar 42 has at its distal end a mating segment 41 which is used to attach the stabilizer attachment either to a traction device or another relatively immovable object. A stabilizer bar 42 also has a distancing segment 43 to distance the mounting segment 44 at a position suitable for patient positioning.

Figure 4:
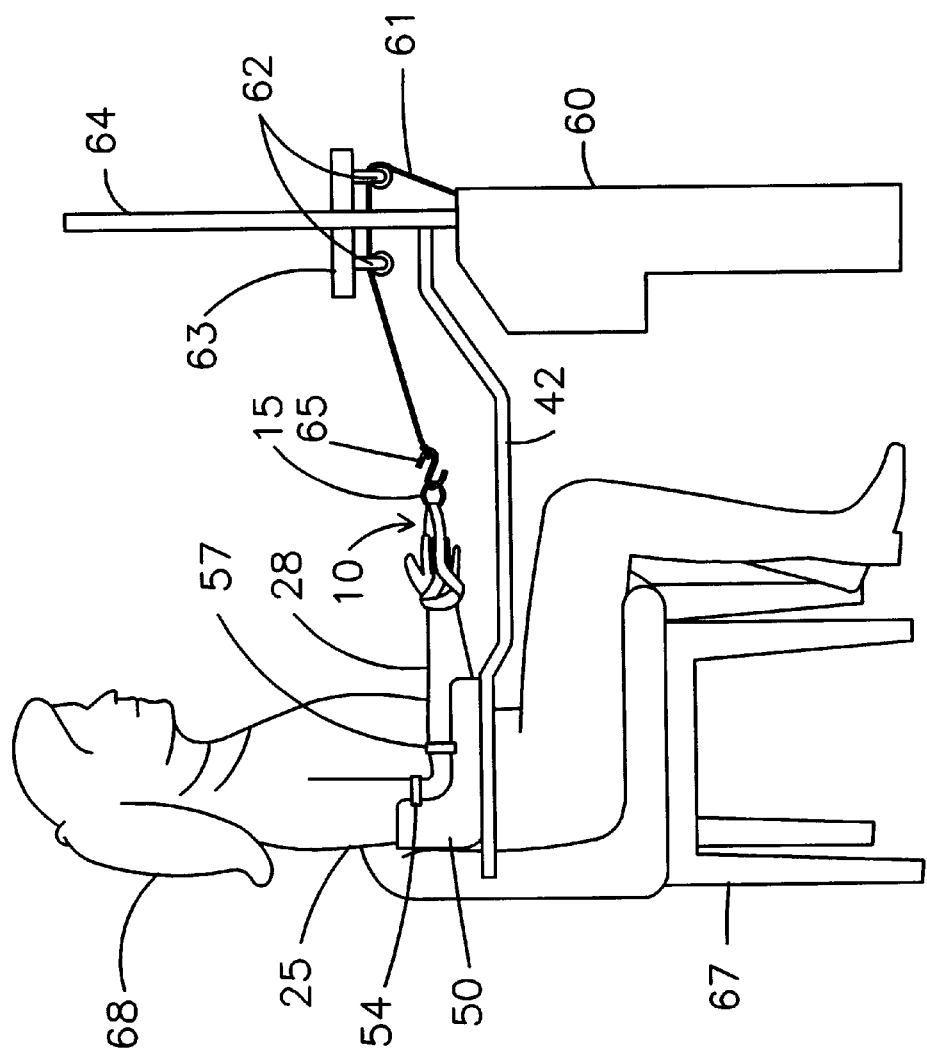
FIG. 4 is a side view of an embodiment of the invention connected to a traction device and in use on a patient.

Mounting segment 44 is secured to elbow cup 50 which generally conforms to the shape of a patient's bent elbow. Elbow cup 50 is adapted to receive an elbow pad 53 which is preferably comprised of covered foam padding. Elbow cup 50 also has two upper arm strap holes 51 and two lower arm strap holes 52. Upper arm strap 54 can be passed through upper arm strap holes 51 and the first strap end 55 secured to second strap end 56 to secure the patient's upper arm in the elbow cup 50. Securing the patient's upper arm 25 in this fashion, as shown in FIG. 4, will isolate the patient's shoulder from the traction device. Applying traction to the patient's shoulder might cause injury to that joint.

Similarly, lower arm strap 57 can be received through lower arm strap holes 52 and first lower arm strap end 58 fastened to second arm strap end 59 to at least partially restrain the patient's lower arm 28 (shown in FIG. 4) and thereby reduce any tension applied by the traction device to the patient's elbow. The elbow is generally a more stable joint than the shoulder, so complete isolation from the traction device is not as critical with this joint.

FIG. 4 shows the preferred embodiment of the present invention in use with a traction device 60. Traction device 60 exerts tension on cord 61 which proceeds through pulleys 62 mounted on adjustable height cross bar 63 to S-hook 65, which in turn is fastened to O-ring 15 on harness 10. The harness 10 in turn engages the patient's hand 29. Adjustable bar 63 can be raised and lowered on vertical bar 64 so that the angle of traction applied by cord 61 is appropriate for the patient's position. Patient 68 is shown sitting in chair 67 with upper arm 25 secured in elbow cup 50 by upper arm strap 54 and lower arm 28 secured in elbow cup 50 by lower arm strap 57.

In practice, a programmable traction device such as the TX-7 Mobile Traction Unit or TX-8 Stationery Traction Unit manufactured by Chattanooga Group, Inc. is preferred. A typical treatment will apply traction for a ten-minute period consisting of cycles of thirty seconds of traction and fifteen seconds of rest. In typical cases, between seven and twenty pounds of traction will be applied to the patient's wrist, depending upon the patient's condition. Daily treatment in accordance with the present invention over a period of two months has resulted in significant diminution of carpal tunnel syndrome symptoms in patients.

While particular embodiments of the present invention have been illustrated and described, it would obvious to those skilled in the art that various other changes and modification can be made without departing from the spirit and scope of the invention. It is therefore intended to cover in the appended claims all such changes and modifications that are within the scope of the invention.

We claim:

1. A method for applying traction to a patient's wrist, between said patient's hand and arm, comprising the steps of:

(a) substantially immobilizing a section of the patient's arm between the patient's shoulder and wrist thereby isolating the patient's shoulder from traction;

(b) placing a harness on an external portion of the patient's hand;

(c) connecting the harness to a traction device; and (d) activating said traction device to apply a traction force to the harness;

wherein a stabilizing attachment for the traction device is used to immobilize a section of the patient's arm between a portion of the upper arm and a portion of the lower arm, said stabilizing attachment having an elbow cup and at least one stabilizing strap capable of restraining the patient's elbow.

2. The method of claim 1 wherein the harness comprises:

(a) a first loop section which encircles the patient's wrist where the wrist joins the patient's hand;

(b) a strap proceeding from said first loop section along and beyond the anterior of the patient's hand, said strap then bending and proceeding back along the posterior of the patient's hand;

(c) a second loop section which encircles the patient's wrist where it joins the patient's hand, said second loop section being connected to the strap along the posterior of the patient's hand.

3. The method of claim 1 wherein the traction device is adjusted to provide between about 7 pounds and about 20 pounds of traction.

4. The method of claim 3 wherein the traction device is a programmable device.

5. The method of claim 4 wherein said traction device is programmed to apply alternating intervals of 30 seconds of traction and 15 sections of rest.

6. The method of claim 5 wherein the traction device is programmed to provide alternative intervals of traction and rest of a total duration of approximately ten minutes.

7. The method of claim 1 wherein the the stabilizing attachment further comprises a mating segment connecting said stabilizer attachment to a relatively immovable object.

8. An arm stabilizer attachment for a therapeutic wrist traction device comprising:

(a) a mating segment which attaches the stabilizer attachment to the traction device;

(b) a stabilizer bar having a distal end and connected to the mating segment, and a proximal end;

(c) an elbow cup mounted on the stabilizer bar near said proximal end, said elbow cup capable of receiving and restraining the patient's elbow;

(d) at least one securing strap capable of securing a patient's arm in said elbow cup, (e) whereby said elbow cup and said at least one securing strap act to prevent the transmission of therapeutic traction forces to the patient's shoulder.

9. The stabilizer attachment according to claim 8 wherein the stabilizer bar is comprised of a distancing segment at its distal end and a mounting segment at its proximal end.

10. The stabilizer attachment according to claim 8 wherein the elbow cup has an inner fitting foam pad.

11. The stabilizer attachment according to claim 8 wherein the elbow cup has a pair of opposed openings to receive an arm securing strap.

12. The stabilizer attachment of claim 8 further comprising a mating segment connecting said stabilizer attachment to a relatively immovable object.

* * * * *